United States Patent [19]

Ridler et al.

[11] Patent Number: 4,685,475
[45] Date of Patent: Aug. 11, 1987

[54] MONITORING ROD

[75] Inventors: Keith D. Ridler, Manchester; Peter J. Taylor; John Poley, both of Royston; Christopher W. Norvall, Southampton; John Upton, Cambridge, all of United Kingdom

[73] Assignee: British-American Tobacco Company Limited, London, England

[21] Appl. No.: 676,173

[22] Filed: Nov. 29, 1984

[30] Foreign Application Priority Data

Dec. 10, 1983 [GB] United Kingdom ............... 8333050

[51] Int. Cl.4 ................................................ A24C 5/32
[52] U.S. Cl. ................................. 131/84.1; 131/280; 131/906
[58] Field of Search ................ 131/906, 280, 84.1

Primary Examiner—V. Millin
Attorney, Agent, or Firm—Kane, Dalsimer, Kane, Sullivan and Kurucz

[57] ABSTRACT

Cigarette rod or cigarette filter rod comprising an outer, longitudinally seamed wrapper is monitored, to detect defects in the longitudinal seam, by directing, from a nozzle, a stream of air tangentially of the rod, whereby the air flows in Coanda effect contact with the rod, and audio detecting the presence or absence of air, at a location spaced from the nozzle, in accordance with the presence or absence of a seam defect.

7 Claims, 4 Drawing Figures

MONITORING ROD

This invention relates to the monitoring of rod, cigarette rod or cigarette filter rod for example, while the rod is moving in an axial direction.

An optical device for monitoring cigarette rod or cigarette filter rod is disclosed in United Kingdom Patent Specification No. 1,388,189. An optical device for monitoring the assembly of filtr tipped cigarettes is the subject of United Kingdom Patent Specification No. 1,474,454.

A device for detecting loose ends or missing filters in cigarettes is described in U.S. Pat. No. 3,720,311. In operation of the device an air stream is impinged against an end face of each cigarette. In the case of a loose end or a missing filter, the resultant turbulence of the air stream produces a distinctive sound the intensity of which is measured by use of a microphone. A somewhat similar device, for detecting the same type of faults in cigarette construction, is described in U.S. Pat. No. 3,863,491. However, whereas in the device of U.S. Pat. No. 3,720,311 an air stream is directed against an end face of each cigarette, in the device of U.S. Pat. No. 3,863,491 an air stream is directed against the side of each cigarette adjacent the end thereof. Because the air stream is directed against the side of each cigarette, in the event of a cigarette having a loosely filled end or a missing filter, the air stream will deform the cigarette inwardly. When such deformation occurs, the air stream is deflected to a region to which it does not pass if the cigarette end is of acceptable formation. A microphone is positioned in the aforementioned region to detect the occurrence of a cigarette deformation.

It is an object of the present invention to provide apparatus which is operable to reliably monitor wrapped rod and to detect defects in the longitudinal lap seam of the wrapping of the rod.

The present invention provides rod monitoring apparatus comprising nozzle means locatable adjacent a longitudinal travel path of rod and operable when thus located to direct a stream of gaseous medium transversely of said path towards the periphery of rod travelling in said path, duct means locatable so that an inlet end thereof can receive gaseous medium of a stream thereof emanating from said nozzle means after the stream has flowed in Coanda effect contact with the periphery of said rod, and a microphone in communication with said duct means.

Preferably the nozzle is operable to direct the stream of gaseous medium substantially tangentially to the peripheral surface of the rod. Advantageously the nozzle means comprises a slit-form exit orifice the major dimension of which is substantially parallel to the rod path when the nozzle means is located in the operable position thereof. A sharp-edge noise generator is suitably incorporated at the duct means and/or the passage means. With a view to substantially preventing, or at least significantly reducing, the incidence of dust or debris being carried onto the microphone by the stream of gaseous medium, the communication of the microphone and the duct means may be via passage means opening from the wall of the duct means and extending to the microphone.

In order that the invention may be clearly understood and readily carried into effect, reference will now be made, by way of example, to the accompanying diagrammatic drawings, in which.

Figure 1:
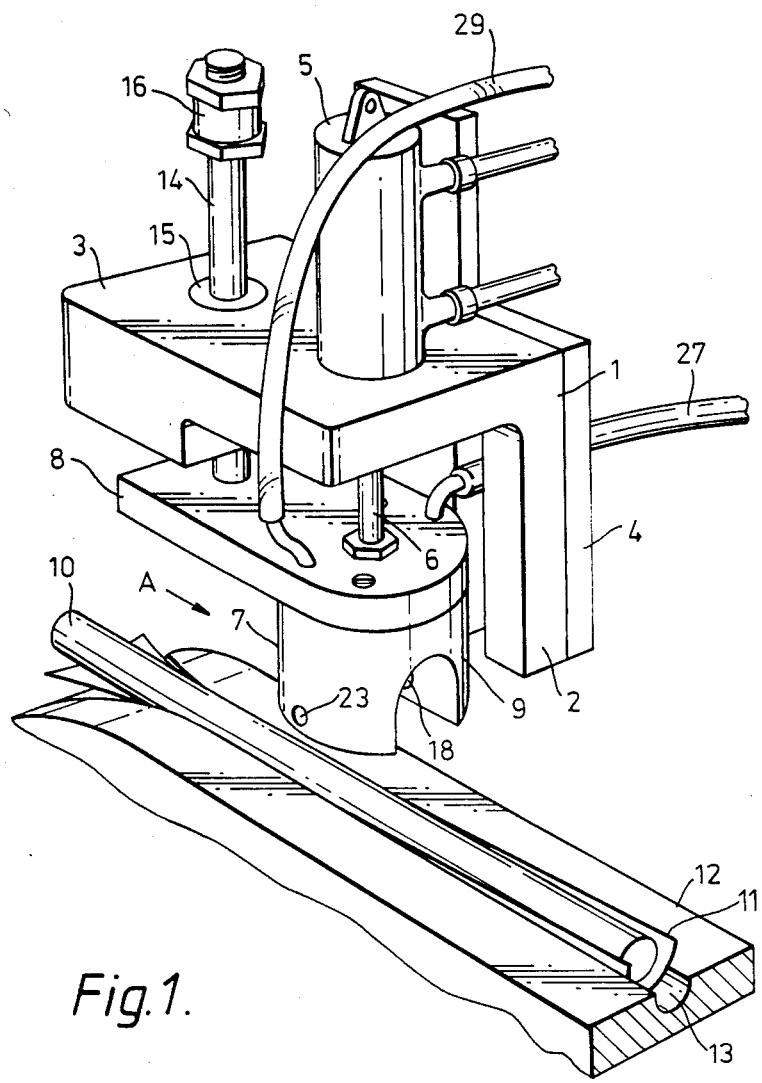
FIG. 1 shows a perspective view of rod monitoring apparatus.

The rod monitoring apparatus shown in FIG. 1 comprises a bracket 1 formed with a vertical limb 2 and a horizontal limb 3. The vertical limb 2 is mounted on a plate member 4 of a cut-off housing, for the sake of simplicity not further detailed, of a cigarette making machine. Carried at the upper side of the horizontal limb 3 of the bracket 1 is a double acting pneumatic cylinder 5, the ram 6 of which extends vertically downwardly through a clearance hole (not shown) in the limb 3. Secured to the ram 6 at the lower end thereof is a monitoring head unit 7 comprising a plate 8 and a monitoring head 9 secured to and disposed beneath a portion of the plate 8. The construction of the monitoring head 9 is shown in greater detail in FIGS. 2 and 3.

In FIG. 1 the monitoring head unit 7 is shown in a raised position. Under action of the double acting pneumatic cylinder 5 the unit 7 may be brought to a lower, operative position, in which latter position the head 9 is located in the proximity of continuous cigarette rod, designated 10, just downstream of the outlet end of the garniture (not shown) of the cigarette making machine. Reference numeral 11 designates a downstream end portion of the upper run of a garniture tape on which the rod 10 rests as it passes beneath the monitoring head 9. Reference 12 designates a portion of a bed which serves to support the rod 10 and tape 11. A groove 13 formed in the upper surface of the bed 12 and extending longitudinally thereof serves to locate the cigarette rod 10 laterally of the bed 12. Cigarette rod 10 is indicated in broken line in FIG. 2 in the position it occupies relative to head 9 when unit 7 is in the operative position thereof.

Secured in the plate 8 of the monitoring head unit 7 and extending upwardly therefrom is a guide rod 14 which is received as a sliding fit in a bush 15 mounted in the limb 3 of the bracket 1. A stop member 16 engages with a screw threaded upper portion of the rod 14, the position of the member 16 being adjustable in order to vary the length of downward movement of the monitoring head unit 7 which can take place before the stop member 16 abuts the upper end of the bush 15 and thus prevents further downward movement of the unit 7.

The monitoring head 9 is formed from a short length of round section metal stock. A slot 17 opening at the lower face of the head 9 extends therethrough, the slot 17 being of sufficient depth and width to enable the head 9 to straddle the cigarette rod 10 when the head 9 is at its lowermost position. As may be observed from FIG. 2, there is a considerable clearance between the rod 10 and the curved upper part of the slot 17.

A length of metal rod 18, providing a nozzle member, is received as a force fit in a bore 19 opening at a vertical wall of the slot 17. The bore 19 extends slightly upwardly, at an angle of 2° say to the horizontal, in a direction towards the slot 17. An axially extending saw cut 20 in the rod 18 is at one end open to the slot 17 and at the other end communicates with a vertical bore 21 formed in the rod 18. There is thus provided a slit-form exit orifice the major dimension of which is parallel to the axis of the cigarette rod 10. The bore 21 communicates with an upwardly extending bore 22 in the head 9, which bore 22 comprises an upper portion 22' of a wider section which opens at the upper surface of the head 9.

Opening from the vertical wall of the slot 17 opposite the bore 19 is a bore 23 which extends horizontally to and opens at the peripheral face of the monitoring head 9. The axes of the bores 19 and 23 are in a common vertical plane. A vertical bore 24 communicates at its lower end with the bore 23 and at its upper end opens into a chamber 25 which is open at the upper surface of the head 9.

Within the chamber 25 there is disposed a condenser microphone and amplifier unit 26.

An end of an air line 27 is received in a bore 28 which extends through the plate 8 and communicates at its lower end with the bore 22 of the monitoring head 9. A cable 29 for supplying powr to the amplifier of the microphone/amplifier unit 26 and for conducting signals from the unit 26 passes to the unit 26 via a bore 30 extending through the plate 8.

Figure 2:
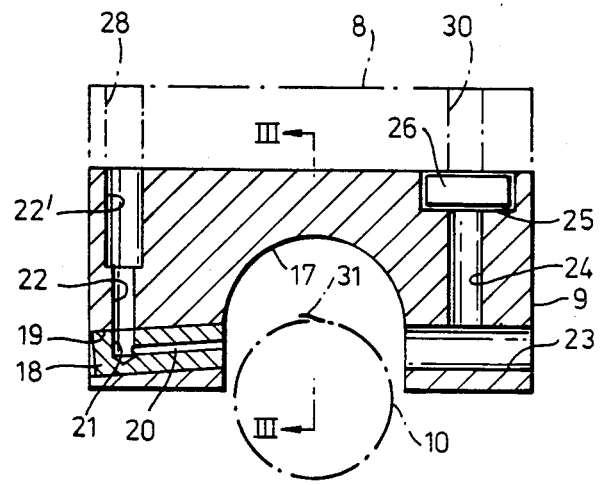
FIG. 2 shows a cross-sectional elevation of a monitoring head of the apparatus of FIG. 1 looking in the direction of arrow A of FIG. 1, the cross-section being taken at line II—II of FIG. 3.
Figure 3:
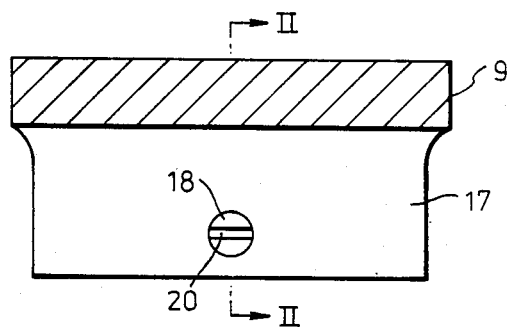
FIG. 3 shows a cross-sectional view of the monitoring head, taken at line III—III of FIG. 2.

In operation of the rod monitoring apparatus to monitor the lap seam, designated 31 in FIG. 2, of the moving cigarette rod 10, air under pressure, of 3 p.s.i.g. for example, is supplied to the saw cut 20 of the nozzle member 18 from the air line 27. The air stream which issues from the saw cut 20 impinges on the peripheral surface of the cigarette rod 10 almost tangentially and then flows in Coanda effect contact with the peripheral surface of the rod 10. When the lap seam of the cigarette paper wrapper of the rod 10 is good, a proportion of the air enters the bore 23 whence it flows to atmosphere at the open outer end of the bore 23. The acoustic noise generated by the passage of air along the bore 23 and across the lower end of the bore 24 is detected by the microphone of the microphone/amplifier unit 26.

When over a length of the cigarette rod 10 the lap seam is not properly made so that the upper of the overlapping portions of the cigarette paper is spaced from the lower overlapping portion or is brought from contact therewith under action of the air stream issuing from the saw cut 20, the Coanda effect contact of the air stream with the rod 10 is disrupted. This condition results in a change in the nature of the signal emitted by the unit 26.

The cigarette rod issuing from the garniture of a modern cigarette making machine is travelling at a considerable speed, 300 meters per minute for example. Thus the ability of the monitoring apparatus to detect a fault extending for a short length only of the lap seam depends on the existence of high frequency components in the signal detected by the microphone of the unit 26 during periods when the lap seam is good. High frequency components are engendered by passage of air across the sharp-edge noise generator formed at the junction of bores 23 and 24. Since the presence of these high frequency components tends to be obscured by lower frequency components, the latter in the signal emitted from the unit 26 are removed by means of an electronic high pass filter. The signal at the output of the filter is composed of a band of frequencies centered on, for example, 6 kHz.

The signal from the filter is subjected to full wave rectification to produce, when the lap seam is good, a continuous train of positive pulses. A monostable device is arranged to be triggered by each pulse. The output of the device remains in a high state so long as the device is retriggered by the next succeeding pulse of the continuous train. However, if a fault occurs in the lap seam the air flow to the bore 23 is interrupted and the device will not be retriggered. In this event the output of the device changes to a low state. This provides an indication of the existence of the fault. As soon as a noise pulse arrives at the device upon the resumption of good seam, the monostable device is retriggered.

The just referred to monostable device may be arranged to trigger a second such device, the two devices being logically OR'ed to operate a fault indicator, a lamp for example. This ensures that the fault indicator is held in a fault indicating condition for a perceptible length of time even if the seam fault is only detected for a length of time imperceptible to the cigarette making machine operator.

The rod monitoring apparatus is capable of detecting faults in the lap seam of the rod 10 which faults are as short in longitudinal extent as about 2 mm and as short in height as 0.5 mm.

In the event of a machine stoppage the monitoring head unit 7 is automatically raised to its upper position by operation of the pneumatic cylinder 5. After the fault causing condition has been rectified and the machine has been restarted, the cylinder 5 moves the unit 7 back down toits operative position, but only after the machine has attained 90% of its full running speed.

Figure 4:
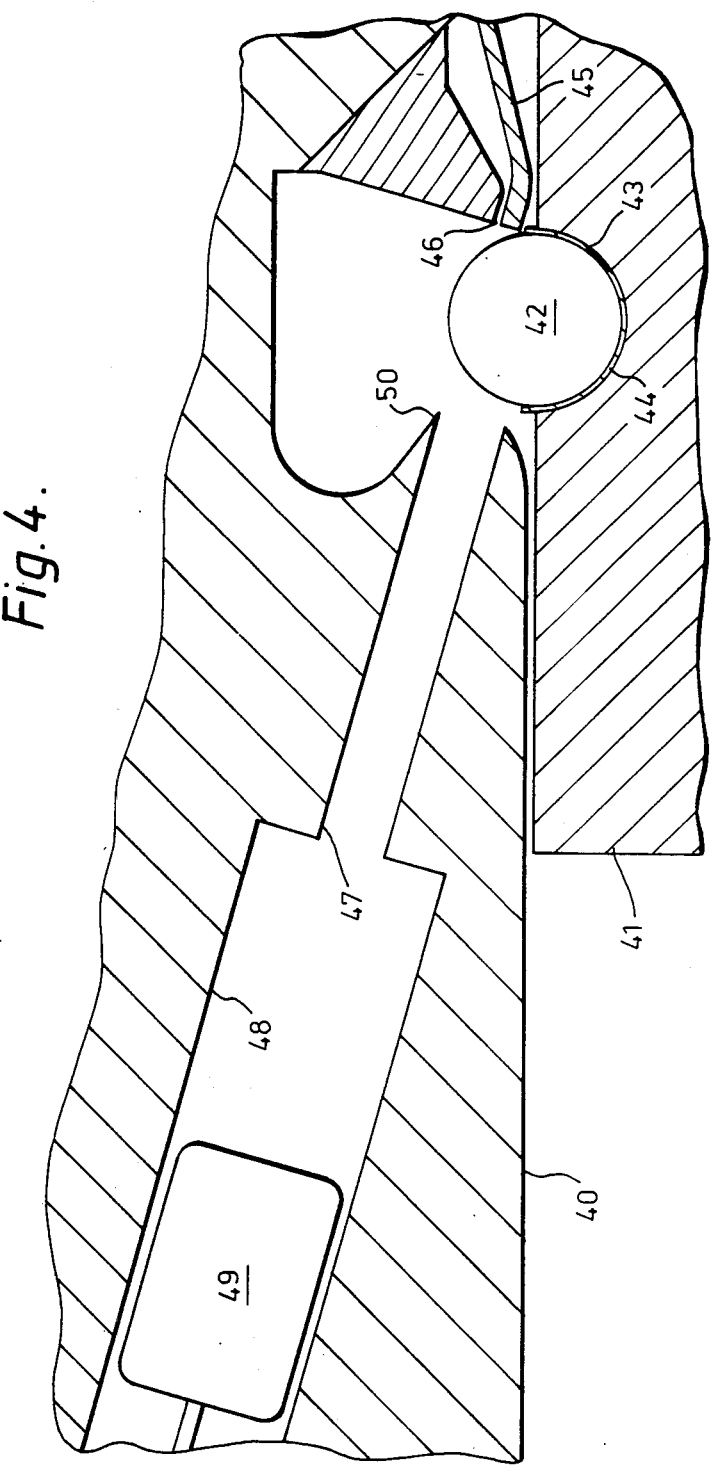
FIG. 4 shows a sectional view of an alternative form of rod monitoring apparatus.

The alternative rod monitoring apparatus of FIG. 4 comprises a body part 40 which is shown located closely above a bed 41 forming part of a garniture assembly of a cigarette making machine. Reference numeral 42 designates a cigarette rod supported on a garniture tape 43 received in a groove 44 in the bed 41. A nozzle 45 comprises a slit-form exit orifice 46 from which an air stream may be directed at the peripheral surface of the cigarette rod 42.

To the side of the path of the rod 42 distant the orifice 46 there opens a duct 47 which extends to a larger diameter bore 48 in which is housed a microphone 49. A noise generator is constituted by a sharp edge 50 extending around the mouth of the duct 47.

The duct 47 and the bore 48 constitute an acoustic chamber which can be tuned by adjustment of the position of the microphone 49 in the chamber 48.

Although in each above described rod monitoring apparatus it is arranged that the air flows past the detector means, e.g. bore 24 and unit 26, during periods when the seam is good, it could alternatively be arranged for the air to flow to or past the detector only in the event that the Coanda effect flow of the air is disrupted by the presence of a seam fault.

What is claimed is:

1. Rod monitoring apparatus for monitoring for defects in a longitudinal lap seam of a wrapper of a moving cigarette rod, said apparatus comprising nozzle means locatable adjacent a travel path of cigarette rod and operable when located to direct a stream of gaseous medium transversely of said path towards the periphery of cigarette rod travelling in said path, duct means locatable so that an inlet end thereof can receive gaseous medium of a stream thereof emanating from said nozzle means after the stream has flowed in Coanda effect contact with the periphery of said rod, and a microphone in communication with said duct means, wherein defects in the longitudinal lap seam of the wrapping of said rod are detected by differences in the acoustic noise pattern of said medium at said microphone.

2. Apparatus as claimed in claim 1, wherein said nozzle means is operable to direct said stream of gaseous medium substantially tangentially to the peripheral surface of rod located at said travel path.

3. Apparatus as claimed in claim 1, wherein said nozzle means comprises a slit-form exit orifice the major dimension of which is parallel to said travel path when said nozzle means is operably located adjacent said path.

4. Apparatus as claimed in any one of claims 1, wherein passage means opening from the wall of said duct means serves to intercommunicate said microphone and said duct means.

5. Apparatus as claimed in claim 1, wherein said nozzle means, said duct means and said microphone are located in a monitoring head unit.

6. Apparatus as claimed in claim 5, wherein said head unit comprises a downwardly open slot dimensioned to receive with clearance rod located at said travel path.

7. A method of monitoring for defects in a longitudinal lap seam of a wrapper of a moving cigarette rod, wherein a stream of gaseous medium is directed transversely of a travel path of cigarette rod towards the periphery of cigarette rod travelling in said path and audio detection is made of gaseous medium of said stream after the stream has flowed in Coanda effect contact with the periphery of said rod, whereby defects in the longitudinal lap seam of the wrapper of said rod are detected in differences in the acoustic noise pattern of said medium.

* * * * *